United States Patent [19]
Bandurski et al.

[11] Patent Number: 5,201,219
[45] Date of Patent: Apr. 13, 1993

[54] METHOD AND APPARATUS FOR MEASURING FREE HYDROCARBONS AND HYDROCARBONS POTENTIAL FROM WHOLE CORE

[75] Inventors: Eric L. Bandurski; John W. Kearns; Houston B. Mount, all of Tulsa, Okla.

[73] Assignee: Amoco Corporation, Chicago, Ill.

[21] Appl. No.: 546,330

[22] Filed: Jun. 29, 1990

[51] Int. Cl.[5] .......................... G01N 1/22; E21B 49/02
[52] U.S. Cl. ..................................... 73/153; 73/19.01; 73/863.12
[58] Field of Search ............ 73/153, 19.01, 19.02, 73/23.38, 23.41, 863.11, 154, 151; 166/248, 250

[56] References Cited

U.S. PATENT DOCUMENTS

| | | | |
|---|---|---|---|
| 4,106,908 | 8/1978 | Leplat-Gryspeerdt | 23/230 |
| 4,153,415 | 5/1979 | Espitalie et al. | 23/230 |
| 4,229,181 | 10/1980 | Espitalie et al. | 23/230 |
| 4,854,163 | 8/1989 | Mount, II et al. | 73/153 |
| 4,885,540 | 12/1989 | Snoddy et al. | 73/153 |

OTHER PUBLICATIONS

Espitalie, Jr., French Petroleum Institute, "Analyzer of Oil and Gas Shows at Drilling Sites", pp. 126–133.

*Primary Examiner*—Hezron E. Williams
*Assistant Examiner*—Michael J. Brock
*Attorney, Agent, or Firm*—James A. Gabala; Richard A. Kretchmer; Frank J. Sroka

[57] ABSTRACT

A heating probe and collection assembly is provided for evaluating free hydrocarbons and hydrocarbon potential of whole core. In one embodiment, the one or more assemblies are used with a core transport system to provide measures of hydrocarbon potential as a function of depth.

18 Claims, 6 Drawing Sheets

Fig. 5

METHOD AND APPARATUS FOR MEASURING FREE HYDROCARBONS AND HYDROCARBONS POTENTIAL FROM WHOLE CORE

The invention relates to locating hydrocarbon source rock or other strata in the subsurface from which hydrocarbons can be released by thermal extraction or pyrolysis. In one aspect, the invention relates to method and apparatus for releasing and measuring such hydrocarbons from whole core.

SETTING OF THE INVENTION

The pyrolysis of kerogen samples is an important technique in source rock analysis. A sample of rock, generally crushed rock, drill cuttings or extracted kerogen, is heated in a stream of helium. The temperature is gradually raised at a carefully measured rate and expelled hydrocarbon gases recorded with a flame ionization detector. At relatively low temperatures (200°-350° C.) any free hydrocarbons in the sample are volatilized. These hydrocarbons are referred to as $S_1$. With increasing temperature hydrocarbons are expelled from the kerogen. These hydrocarbons are termed $S_2$. Carbon dioxide and water, which are also expelled, are grouped as $S_3$ and can be measured using, for example, a thermal conductivity detector. Pyrolysis generally continues up to 800°-900° C. The three readings can be used to determine the maturation level of the source rock. Where migration has not occurred, the ratio $S_1/(S_1+S_2)$ shows the amount of petroleum generated compared with a total amount capable of being generated. Plotted against depth, this ratio generally shows a gradual increase as the source rock matures. The pyrolysis temperature $T_m$ corresponding to maximum release of hydrocarbons can also be determined.

Most such measurements are taken in the laboratory, although field measurement is also possible. See New Version Rock-Eval. Operation Manual. SocietéDelsi: T. Espitalie, Analyzer of Oil and Gas Shows at Drilling Sites, 02.11/78. Analyses of drill cuttings, while advantageous for many purposes, can only be approximately correlated with subsurface location since any drill cuttings sample is a composite over a range of depths. The heterogeneous drill cuttings sample can also not easily be correlated with a particular stratum. Also, the relatively high surface area to volume ratio of drill cuttings permits loss of volatiles, contamination from drilling fluids, and makes drill cuttings difficult to clean effectively. Additional loss of volatiles can result if the drill cuttings are not analyzed at the well site but are sent to a laboratory for analysis.

Whole core can be taken along substantial portions of a wellbore and can be analyzed for various parameters on-site while the core is fresh and has not lost transient in situ characteristics such as in situ fluids, compression, color and the like. See U.S. Pat. Nos. 4,854,163; 4,885,540; 4,899,219; and 4,911,001.

The invention relates to apparatus and method for determining free hydrocarbons and source rock characteristics of whole core.

The invention relates to a probe and collection assembly for use in such apparatus and method.

The invention relates to a tool comprising two or more such probes and collection assemblies for use in such apparatus and method.

The invention relates to a method and apparatus for determining source rock characteristics of whole core under substantially in situ conditions.

The invention relates to a method and apparatus for determining source rock characteristics of whole core which does not require extensive preparation or destruction of core materials.

SUMMARY OF THE INVENTION

Source rock characteristics relating to free hydrocarbons and hydrocarbon potential are measured from whole core optionally at the well site using core under substantially in situ conditions. Such measurements can be directly correlated to depth, stratum and lithology of the core. From the measurements selected intervals of core can be selected for further analysis. By generating logs displaying such measurements from the core and one or more logs of the well from which the core was taken, the measured source and reservoir rock characteristics can be correlated with intervals of other wells having corresponding subterranean features as indicated by similar log responses.

According to the invention, there is method and apparatus for evaluating free hydrocarbons and hydrocarbon potential of core taken from a wellbore by contacting core surface of the core with a controlled application of heat using a heating probe, heating the heating probe in surface contact with core to a temperature effective for causing release of hydrocarbons from core, and collecting and measuring the released hydrocarbons.

In further aspects, the invention comprises method and apparatus for causing a heating probe and collection assembly to engage core surface, to be controlledly heated for releasing and collecting hydrocarbons therefrom and thereafter to disengage therefrom and for causing the core and the heating probe to move relative to one another such that at successive times successive portions of core surface are available for engagement and engaged by the heating probe and for collection and measurement of hydrocarbons released therefrom.

DETAILED DESCRIPTION OF THE INVENTION

In various aspects, the invention comprises a heat probe for applying heat to a portion of the surface of whole core. The heat probe can be, for example, a laser, a high thermal conductivity probe heated by a heating element and the like.

In various aspects, the invention comprises a collection chamber adjacent the portion of the surface of core to which heat will be applied for collecting hydrocarbons evolved from the surface by the application of heat. The collection chamber can be formed by a cavity within the heat probe opening to the surface of the core or can be a chamber formed adjacent outside the heating probe or can be a structure transparent to laser wavelengths where a laser is used for applying heat to the surface of the core and the like.

The collection chamber preferably includes a seal in sealing engagement with the surface of the core to assure that all or most of the liberated hydrocarbons are trapped by the collection chamber. The seal can be a metal seal formed by the heat probe itself, or other mechanical seal such as graphite, teflon, silicone, rubber and the like, or can be a gas seal formed by flowing gas adjacent the collection chamber to retard escape of released hydrocarbons. The collection chamber is preferably adapted with means for flowing a carrier gas therethrough to absorb and transport the evolved hydrocarbons to a detector, for example, a flame ionization detector or other suitable detector.

The heat probe, collection chamber, and seal can be mounted on a probe assembly which can be adapted to be moved into engagement with the core surface. The probe assembly and the core can also be moved relative to one another to provide measures of free hydrocarbons and hydrocarbon potential at intervals along core. These measures can be displayed as a log of the core as a function of depth.

In various aspects, volatile hydrocarbons are provided from the collection chamber to a detector for detecting the hydrocarbons. The detector can be any suitable detector such as a gas chromatograph, a mass spectrometer, a flame ionization detector, a thermal conductivity detector and the like. A flame ionization detector is preferred for its speed of operation.

These and other aspects of the invention will be apparent from the following detailed description of the drawings.

Figure 1:
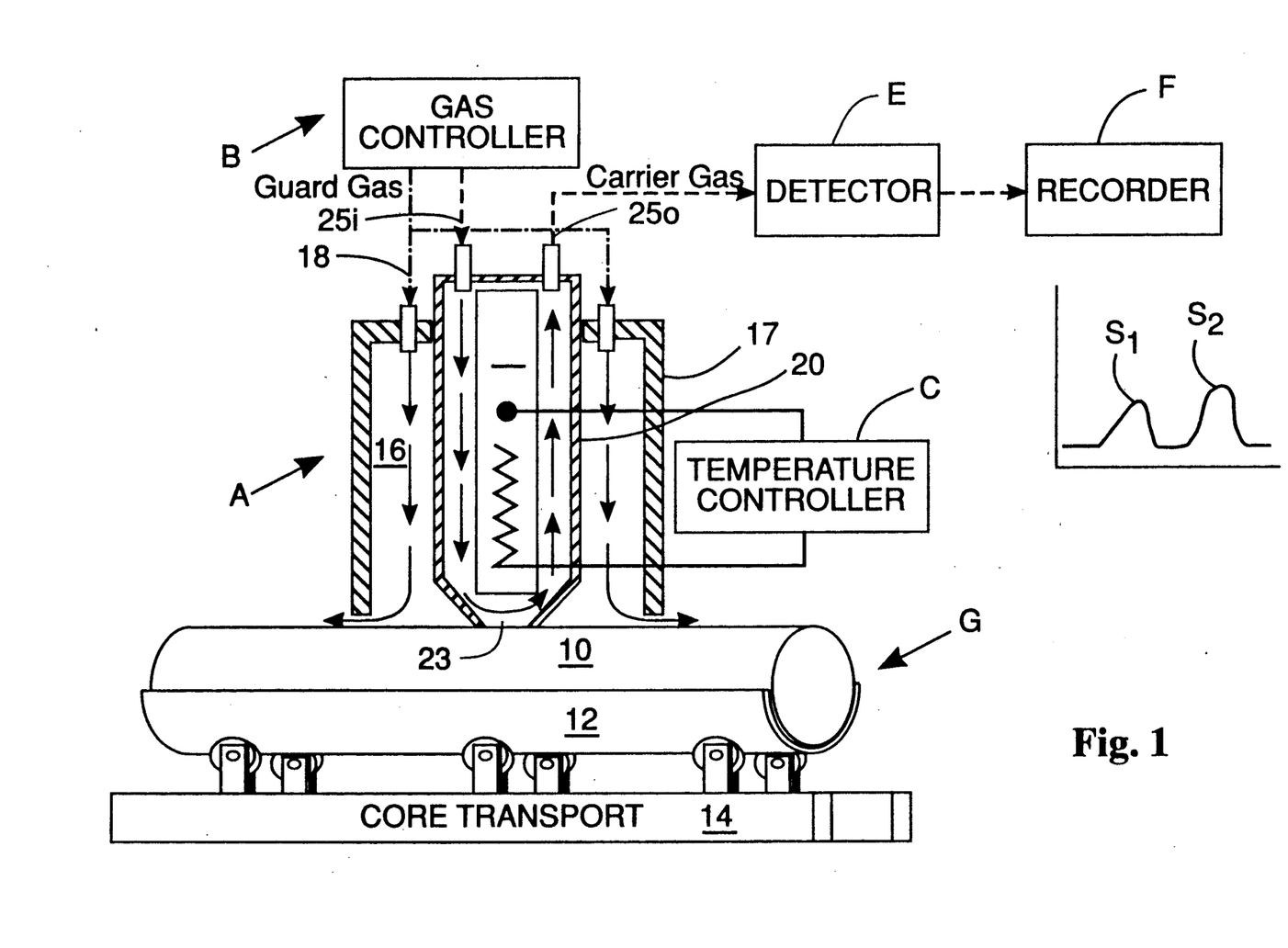
FIG. 1 illustrates schematically apparatus and method for evolving, collecting and analyzing hydrocarbon gases from whole core taken from the earth's subsurface.

Referring now to FIG. 1, FIG. 1 illustrates schematically apparatus and method for evolving, collecting and analyzing hydrocarbon gases by application of heat to whole core taken from the earth's subsurface. Whole core 10 carried by a core holder 12 on a core transport 14 can be transported adjacent a heat probe and collection chamber assembly A. Core 10 is shown in contact with the probe assembly A, but during transport of core either the core or the probe assembly is advantageously removed from contact.

Assembly A comprises heat probe 20 heated by heating cartridge 22 under control of a temperature controller C such as a thermocouple. Probe 20 can be generally cylindrical and formed of heat conductive metal such as brass and can have a core adjacent end or tip which can be urged into contact or even sealing engagement with core 10. A hollow formed within the core-adjacent end of probe 20 can form the collection chamber 23 and a carrier gas can be introduced by line 25i into chamber 23, where it can flow past the heated portion of core 23, absorbing evolved gases and be delivered by line 25o (which can be heated and/or insulated) to detector E (for example, a flame ionization detector) and results recorded by recorder F. Temperature controller C can control the temperature of probe 20 to heat surface of core 10 to a temperature effective for evolving free hydrocarbons (for example, about 350° C.) or to a temperature effective for evolving pyrolysate from kerogen (for example, about 600° C.). Controller C can be used to incrementally heat probe 20 to desired temperatures, but preferably is continuously maintained at effective temperatures so as to reduce time required for release of hydrocarbons when probe 20 is brought into contact with core 10. Free hydrocarbons detected by detector E are recorded by recorder F as peak $S_1$. Hydrocarbons evolved from pyrolysis of kerogen in source rock are represented by peak $S_2$. Other source rock characteristics can also be determined by those skilled in the art using the invented apparatus.

In addition to the mechanical seal formed by the open core adjacent end of probe 20 urged into engagement with core 10, a gas seal can be provided as illustrated by providing a guard gas through peripheral annular space 16 formed by housing 17 which may be made of a heat insulating material such as ceramic, to provide approximately equal pressures of gas on the inside and outside of the core adjacent end of probe 20. Housing 17 can be adapted as illustrated to permit guard gas to escape.

Figure 1A:
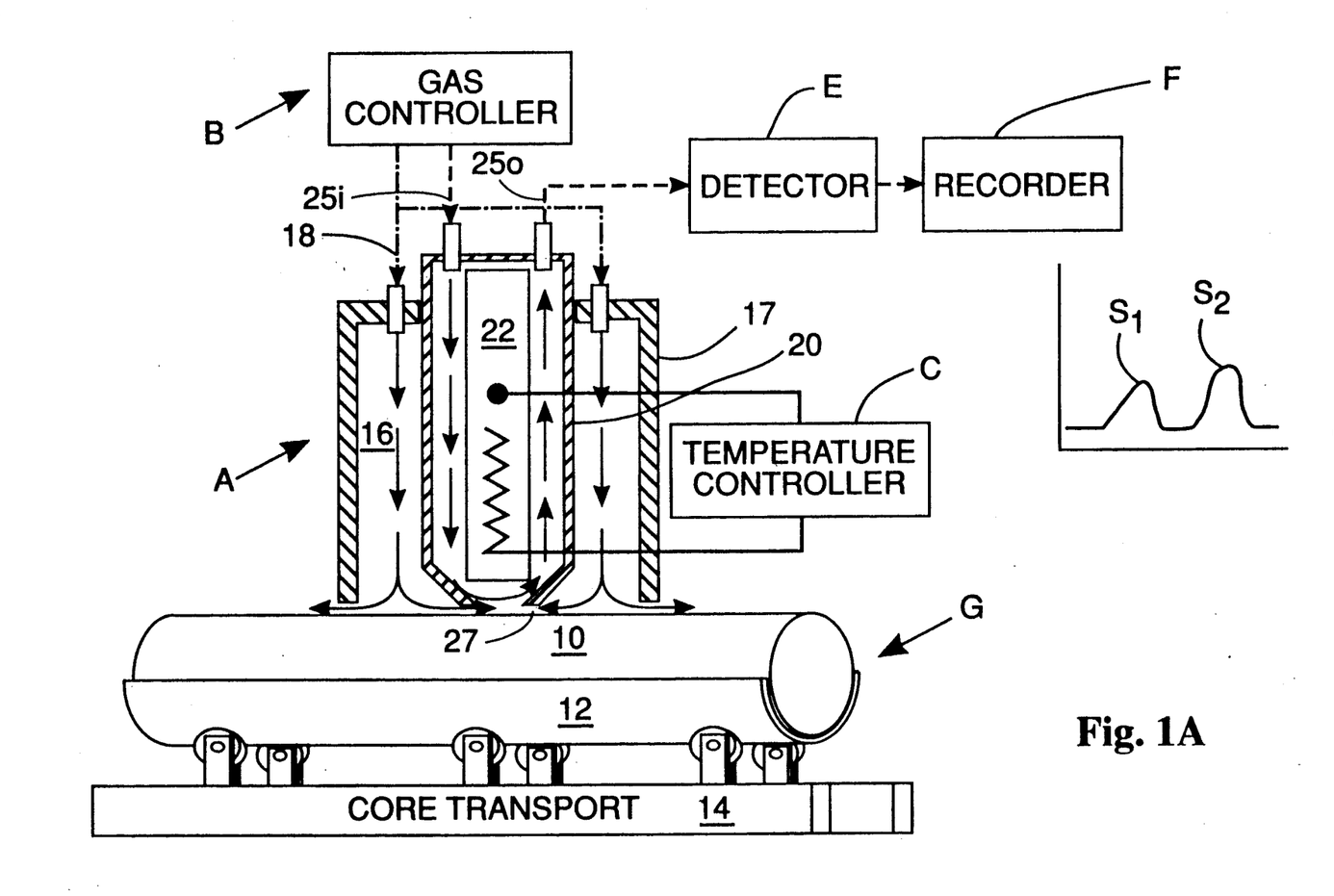
FIG. 1A illustrates an alternative embodiment of FIG. 1.

Referring now to FIG. 1A, FIG. 1A illustrates an alternative embodiment of the FIG. 1 apparatus in which a portion of guard gas is used as carrier gas by introduction into the collection chamber by one or more openings 27 formed in the core-adjacent end of probe 20 and is removed by line 25o to the detector. Other reference numerals correspond to those shown in FIG. 1 and do not require further description here.

Figure 2:
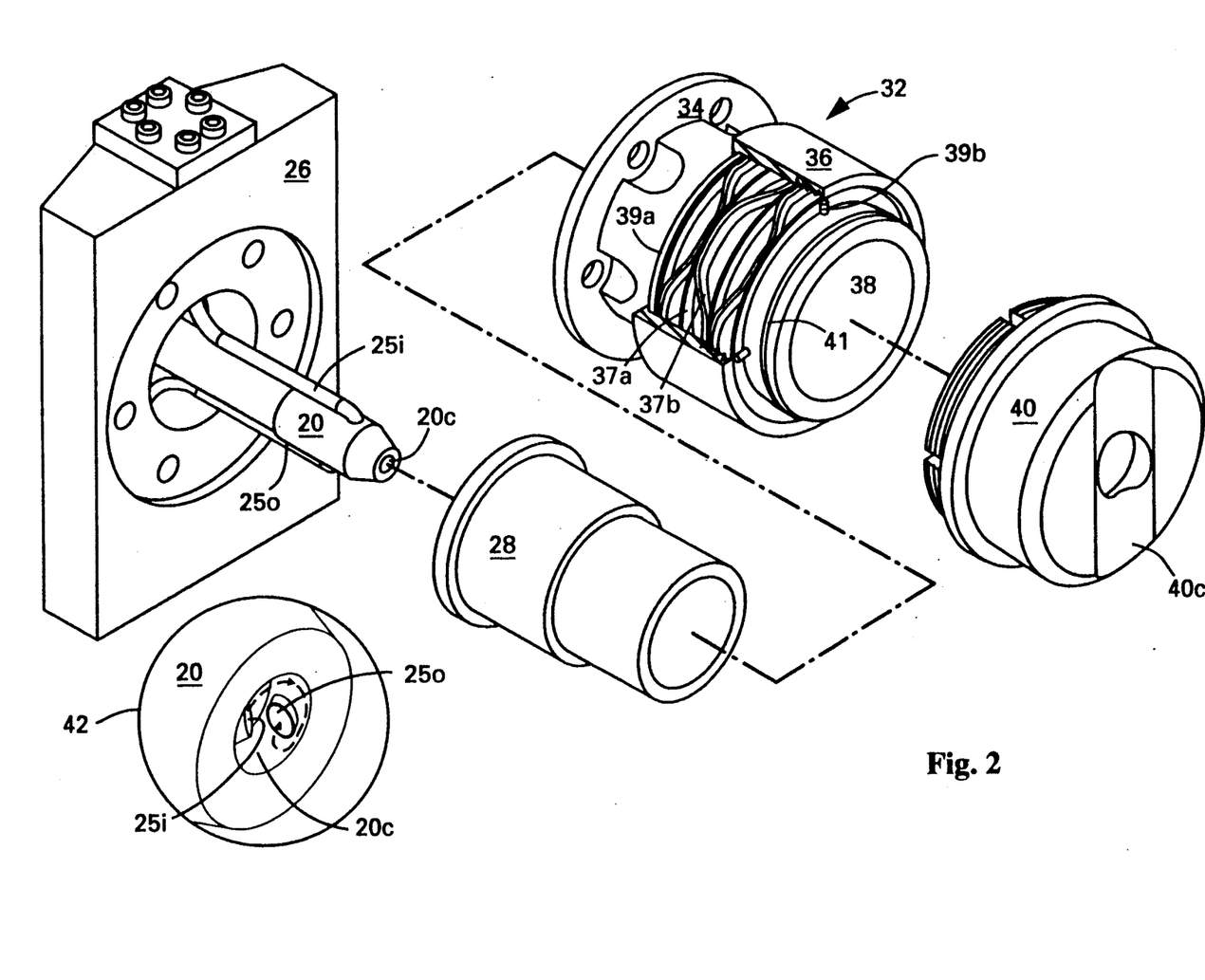
FIG. 2 illustrates in exploded view a first embodiment of the probe and collection assembly A of FIG. 1.

Referring now to FIG. 2, FIG. 2 shows in exploded view and in greater detail a preferred embodiment of the probe and collection assembly A of FIG. 1. As illustrated, a probe 20 having carrier gas provided via line 25i and removed via line 25o can be mounted to mounting block 26. Probe 20 has a collection chamber 20c formed in its core-adjacent end.

Referring to circle 42, circle 42 illustrates in enlarged view the interior of the collection chamber 20c formed in the tip of probe 20. Carrier gas can be introduced by line 25i in tangential flow to create a swirling flow of gas in collection chamber 20c to outlet line 25o. A generally cylindrical ceramic guard chamber 28 forms a heat insulating sheath which can be received by mounting block 26 to define between the interior of the ceramic guard 28 and probe 20 a guard chamber 16 through which guard gas flows at about the same pressure as occurs within the collection chamber. The heat insulating sheath is particularly advantageous while probe 20 is maintained continuously at effective thermal extraction or pyrolysis temperatures.

A retractable probe guard assembly 32 having base 34 can receive ceramic guard 28 therewithin and can be mounted to mounting block 26. Assembly 32 can have a retractable sleeve 36 equipped with leaf springs 37b and shims 37a constrained by slip ring 39a and pins 39b to permit movement of retractable sleeve 36 responsive to pressure exerted by the probe assembly against a core or conversely. A nose guard 40 can be threadably received on the end of the retractable sleeve 36. A high compression ring 41 provides a seal therebetween. As illustrated, the nose guard 40 can be adapted with a concave portion 40c adapted to receive the convex outer surface of core 10 assuring effective seating of the probe and collection assembly A on the core. When the probe assembly A is brought into contact with the surface of the core 10 as illustrated in FIG. 1, the retractable sleeve 36 and attached nose piece 40 retracts and permits probe 20 in sleeve 28 to contact the core surface as illustrated in FIG. 1.

Figure 3:
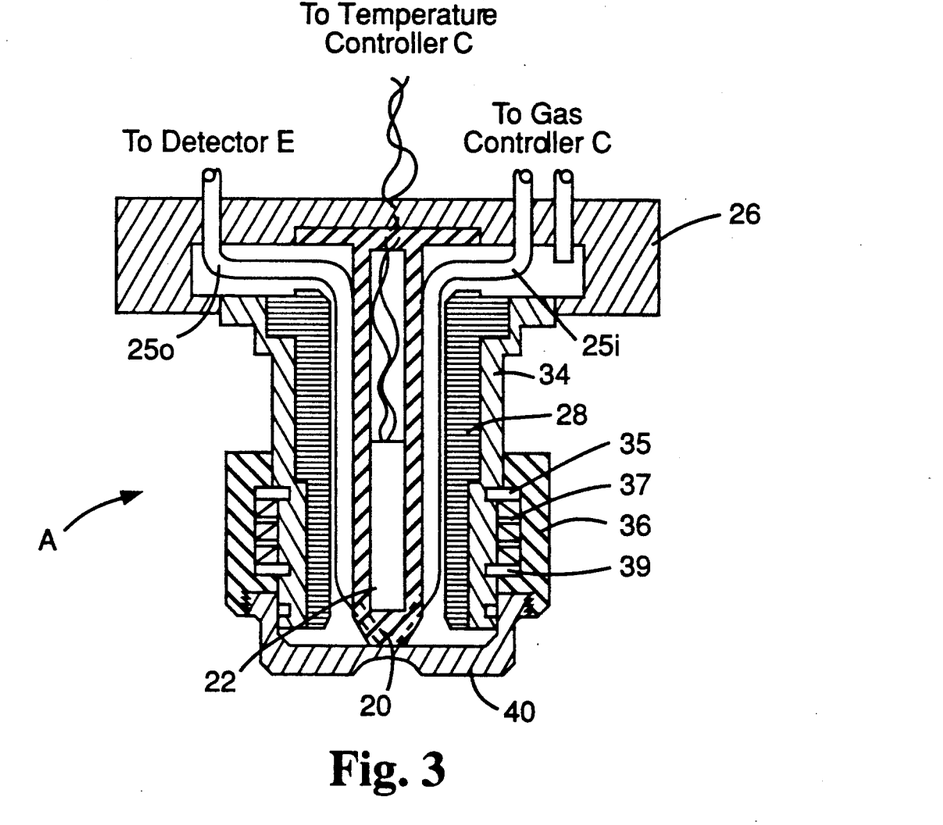
FIG. 3 illustrates in plan view a section through the probe and collection assembly of FIG. 2.

Referring now to FIG. 3, FIG. 3 illustrates in plan view a section through the probe and collection assembly A of FIG. 2 showing mounting base 26 having probe 20 containing heating element 22 mounted therein. Carrier inlet 25*i* is flow connected to a collection chamber formed by hollow region in the tip of the probe by gas fittings to gas controller B (not shown) and carrier outlet 25*o* is flow connected by gas fittings to detector E (not shown). Ceramic guard 28 received by sleeve assembly 34 is also mounted to base 26. Ring 39*a* and pins 39*b* restrain interleaved shims 37*a* and leaf springs 37*b* permitting nose guard 40 and connected retractable sleeve 36 to retract as a unit from the core to permit probe 20 to engage the core surface.

Figure 4:
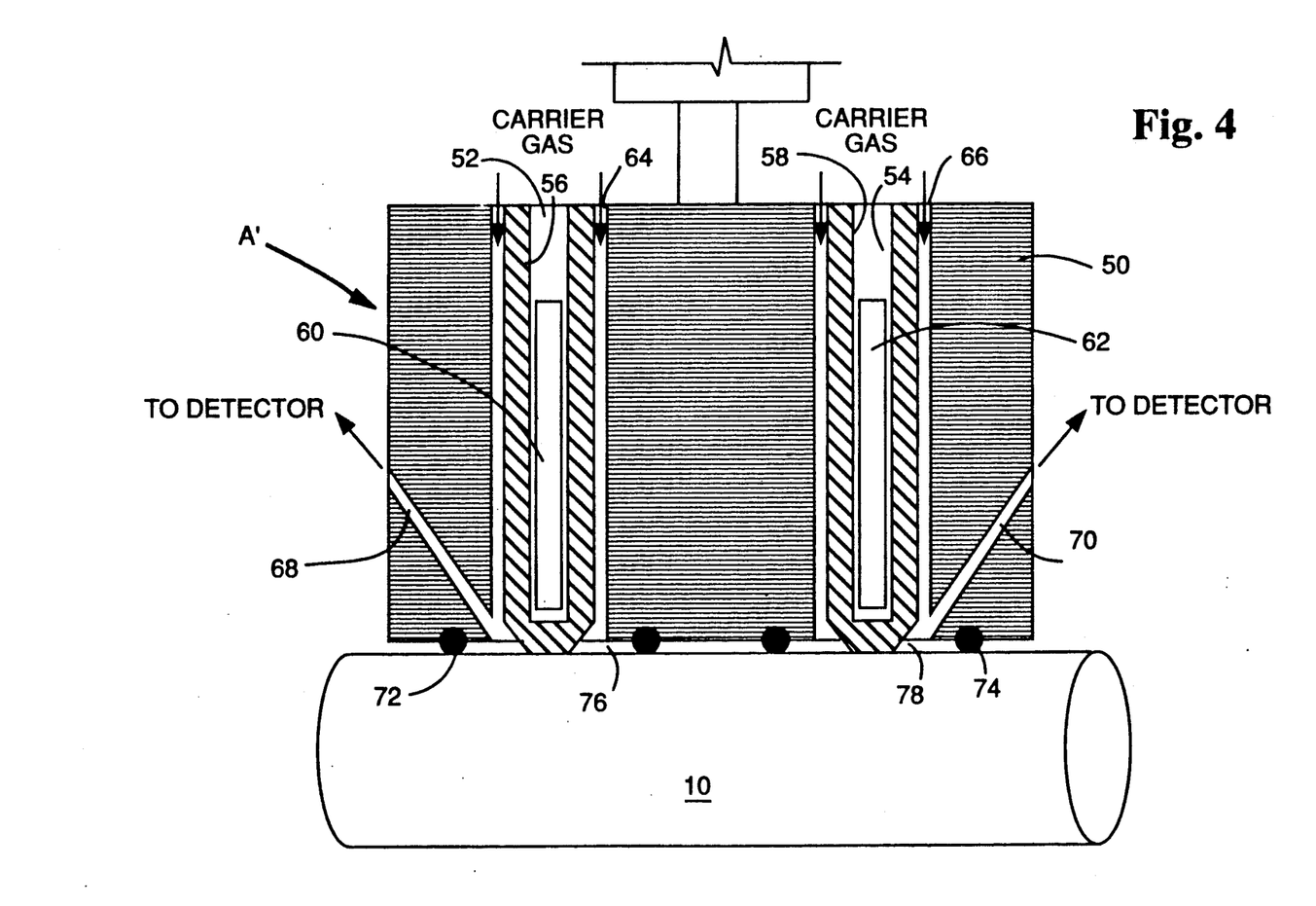
FIG. 4 illustrates an assembly in accordance with the invention having two heating probes and collection chambers.

Referring now to FIG. 4, FIG. 4 indicates that a probe guard and carrier assembly A' can be equipped with more than one probe. Thus, for example, ceramic block 50 can have cylindrical chambers 52 and 54 therein for receiving probes 56 and 58 therein having heating elements 60, 62. Spaces such as annular spaces 64, 66 can be provided permitting carrier gas to flow adjacent the probe-core contact surface to absorb evolved gases. The absorbed gases can be removed via channels 68, 70 to detectors (not shown). As illustrated, mechanical seals 72, 74 such as graphite, a high temperature elastomer or the like O-rings can be used to define collection chambers 76, 78 adjacent the probe-core contact. In this way, first probe 56 can be analyzing core for free hydrocarbons while second probe 58 is concurrently pyrolyzing kerogen and analyzing released hydrocarbons.

Figure 5:
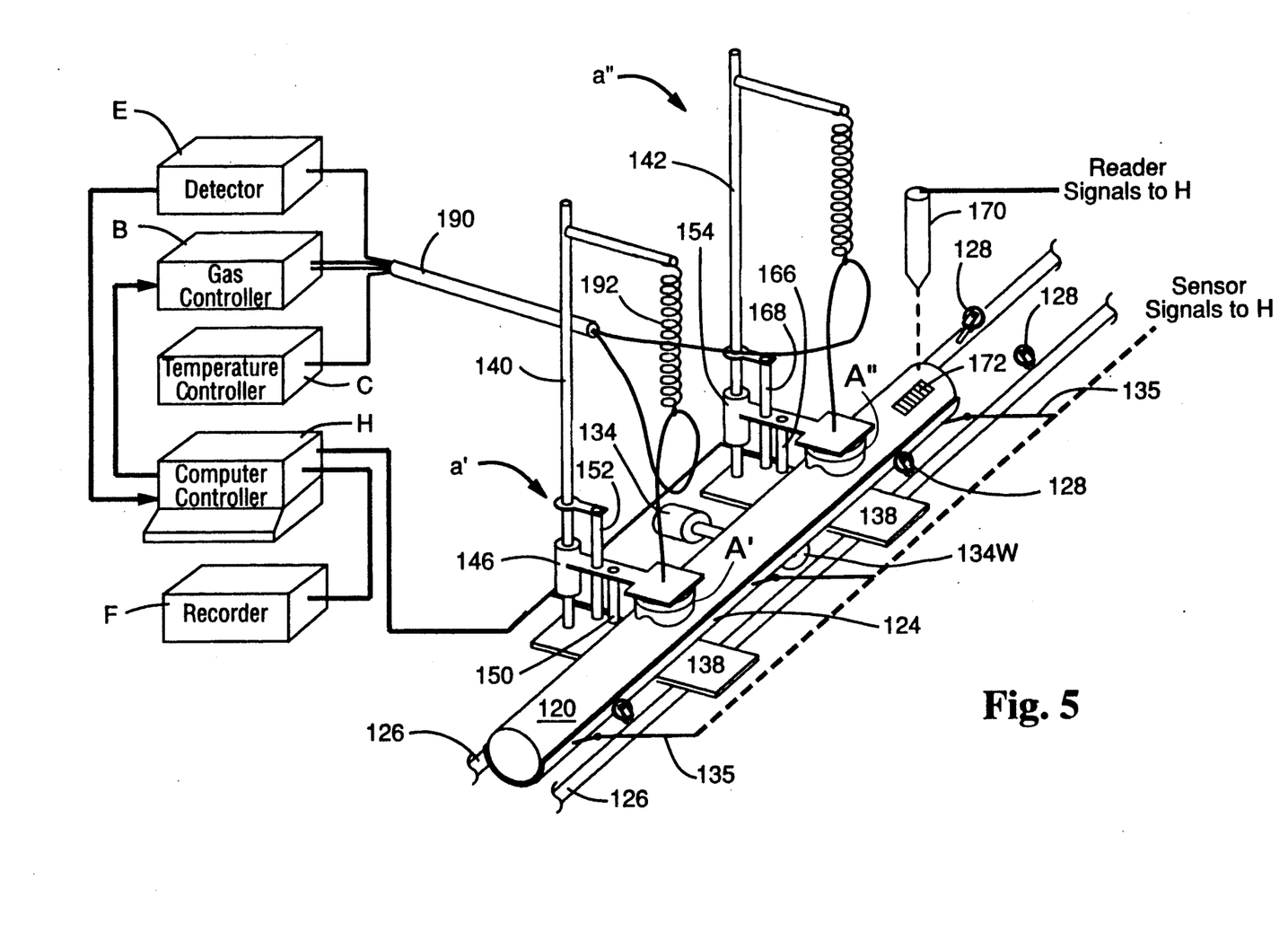
FIG. 5 illustrates an embodiment of the invention comprising two probe and collection chamber assemblies in combination with a core transport system.

Referring now to FIG. 5, FIG. 5 illustrates method and apparatus in accordance with the invention. As shown in FIG. 5 full barrel core 120 is supported, for example, by a semicylindrical core trough 124 and moved in increments by motor 134 having friction drive wheel 134W, responsive to computer/controller H past a free hydrocarbon and source rock evaluation station, preferably dual, and comprising assemblies A' and A''. The core trough is supported by rollers 128 on frame 126 during movement. The core is preferably washed to remove muds and surface particles. See U.S. Pat. No. 4,911,001. If desired, Core surface can be abraded or cut or otherwise treated to expose fresh rock surface.

Core 120 can have a bar code 172 or other indicia of depth affixed thereto to be sensed by a sensor such as bar code reader 170 which can provide the initial recorded depth of the section of core to computer controller H. Position sensors 135 positioned at spaced apart intervals along frame 126 sense presence of the core and together with information relating to the rate of rotation of motor 134 can be used by computer/controller H to provide a record of depth for each hydrocarbon analysis as hereinafter described.

The hydrocarbon and source rock evaluation station preferably comprises two adjacent stations A' and A''. Station A' can be effective for producing a record of free hydrocarbons by controllably heating core surface to a free hydrocarbon evolution temperature range using temperature controller C. Analysis station A'' can be effective for producing a record of $S_2$ by controllably heating to pyrolysate generation range. Alternatively, each station can be used to generate records of both $S_1$ and $S_2$ and other measurements as desired. More than two stations can of course also be used.

Referring now to the analysis station A', the station can comprise support means adjacent translation means such as base plate 136 affixed to the frame 126 for supporting probe and collection assembly A'. Assembly A' can be supported by mount 146 and positioned to be lowered into contact with the core as it is stopped thereboneath. Bearing mount 146 can be supported on rail support 140 for vertical up and down movement of Assembly A' effected by ram 50. Guide slide bar 152 can be provided parallel to rail support 140 to provide additional control for vertical movement of assembly A'. Ram 150 responds to a signal from computer H for bringing assembly A' into contact with the core 120 following each increment of movement. The concave portion of the nose piece (see FIG. 3) assists in seating the probe normal to the core surface. Assembly A' can also be flexibly mounted to bearing mount 146 to facilitate seating. In addition to pneumatic ram 130 and motor 134, station A' can also be controlled by Gas Controller B and Temperature Controller C, as illustrated, via harness 190 flexibly mounted by spring 192 and support 194 to rail support 140 to facilitate up and down movement of Assembly A'.

Second analysis station A'' likewise can comprise a base plate 138 mounted to a frame 126 to which the probe and collection assembly A'' is attached. A guide bar 168 can be provided. Assembly A'' can be mounted by bearing mount 154 to rail guide 142 with guide bar 168 for vertical up and down movement effected by ram 166.

Assembly A'' can be spaced apart from the assembly A' to prevent cross temperature effects, for example, when Assembly A' is at a temperature effective for thermal evolution of hydrocarbons and Assembly A'' is at a temperature effective for pyrolysis. By use of such dual assemblies reservoir rock containing free hydrocarbons can be readily differentiated from source rock.

It will be seen from FIG. 5 that each of the probe collection assemblies A' and A'' and ancillary structures are moved as a unit by their respective rams.

During operation of the invented apparatus, core 120 is moved by motor 134 responsive to a motor control signal from computer/controller H. Control is indicated by letters CC. As core 120 is moved adjacent sensor 170, the initial depth indication 172 is read and a signal provided to computer controller H by sensor 70. As core 120 is moved in increments adjacent the position sensor 136, signals are provided to computer/controller 176 which uses information about the rate of rotation of motor 134 with friction drive 134W to provide a record of depth for each hydrocarbon evaluation as it is made. Computer controller H generates position signals for each measurement and can provide position signals or depth signals together with signals representing the results of analysis by detector E to recorder F where they can be used to generate a continuous record or log of free hydrocarbons and hydrocarbon potential as a function of depth.

Core 120 is preferably moved in discrete increments, for example, with analysis occurring about every three inches to provide a complete record of free hydrocarbons and hydrocarbon potential for core 120. For each increment of movement, each of rams 150 and 166 can be actuated and measurements made.

Under control of computer controller H, temperature, controller C causes one of A', A'' to be at a temperature, for example, of about 350° C. effective for thermal extraction of free hydrocarbons and the other assembly to be at a temperature of, for example, about 600° C. effective for evolution of pyrolysate. Gas controller B provides carrier and guard gas at effective pressures and evolved gases are provided to detector D for analysis. Back flush of the various gas flow lines can also be provided by controller B between times of analysis. Measurements of evolved gases are recorded as a function of depth by recorder F.

It will be appreciated that the invented method and apparatus are particularly useful for field application where a record of hydrocarbon potential of whole core can be made before transient characteristics are lost, but are also suitable for analysis of whole core in a laboratory, storage, or other facility. The method and apparatus of the invention provides a rugged, light and compact system suitable for field use in providing a continuous record of the hydrocarbon potential of core under substantially in-situ or fresh conditions with minimal preliminary preparation of the core.

While the invention has been described in terms of a preferred embodiment, the invention is not limited thereto but by the claims attached hereto and interpreted in accordance with the applicable principles of law.

What is claimed is:

1. Method for evaluating hydrocarbon potential of core taken from a wellbore comprising:
    contacting a portion of core surface of whole core taken from a wellbore with a heating probe comprising a high conductivity heating tip;
    controlling heat applied to the core by the heating probe in surface contact with the portion of surface of whole core to a temperature effective for causing release of hydrocarbons;
    causing at least a portion of released hydrocarbons to flow into a collection chamber; and
    collecting released hydrocarbons.

2. The method of claim 1 further comprising:
    flowing carrier gas from a source thereof to the collection chamber then to a detector and transporting at least a portion of released hydrocarbons from the collection chamber to the detector.

3. The method of claim 1 comprising:
    passing carrier gas through the heating probe into a collection chamber contained therein.

4. The method of claim 1 comprising:
    passing carrier gas adjacent the heating probe and core surface with the heating probe in contact with the core surface effective for absorbing released hydrocarbons.

5. The method of claim 1 comprising:
    causing the heating probe and collection assembly to engage the core surface effective for releasing and collecting hydrocarbons therefrom and thereafter to disengage therefrom.

6. The method of claim 1 further comprising:
    causing the core and the heating probe and collection chamber to move relative to one another such that at successive time successive portions of core surface are available for engagement by the heating probe and for collection of hydrocarbons released therefrom.

7. Apparatus for evaluating hydrocarbon potential of whole core taken from a wellbore comprising:
    a heating probe comprising a high conductivity heating tip for contacting and applying heat only to a portion of surface of whole core taken from a wellbore;
    a temperature controller for controlling heat applied to the core by the heating probe in surface contact with core to a temperature effective for causing release of hydrocarbons from core;
    collection means adjacent the portion of surface of whole core to which heat is applied for collecting released hydrocarbons; and
    a collection chamber adjacent the heating probe including a seal in sealing engagement with the core surface for causing at least a portion of released hydrocarbons to flow into the collection chamber.

8. The apparatus of claim 7 further comprising:
    a source of carrier gas;
    a detector for detecting released hydrocarbons; and
    means for flowing carrier gas from the source to the collection chamber to the detector effective for transporting at least a portion of released hydrocarbons from the collection chamber to the detector.

9. The apparatus of claim 8 wherein:
    the heating probe comprises a core surface contacting portion shaped to form the collection chamber therewithin; and
    the means for flowing carrier gas includes means for introducing carrier gas into the collection chamber and means for removing carrier gas from the collection chamber.

10. The apparatus of claim 9 wherein:
    the means for introducing carrier gas into the chamber comprises a conduit passing through the heating probe into the collection chamber.

11. The apparatus of claim 9 wherein:
    the means for introducing carrier gas into the chamber comprises a conduit formed by the core surface contacting portion of the heating probe and the core surface upon the core surface contacting portion of the heating probe being in contact with the core surface.

12. The apparatus of claim 8 wherein:
    the seal of the collection chamber comprises a gaseous seal formed by flowing a guard gas adjacent the collection chamber and the core surface, the gas having a pressure effective for retarding escape of released hydrocarbons from the collection chamber.

13. The apparatus of claim 12 wherein:
    the pressure of the guard gas adjacent the collection chamber is about equal to the pressure of the carrier gas within the collection chamber.

14. The apparatus of claim 7 wherein:
    the seal comprises a mechanical seal.

15. The apparatus of claim 7 further comprising an insulating sheath adjacent the heating probe.

16. Apparatus for evaluating hydrocarbon potential of whole core comprising:
    a heating probe and collection assembly for contacting, heating and collecting released gases from a portion of core surface of whole core taken from the wellbore, the assembly comprising a heating probe comprising a high conductivity heating tip for contacting and for applying heat only to a portion of surface of the whole core and a collection chamber adjacent the heating probe including a seal in sealing engagement with the core surface for causing at least a portion of released hydrocarbons to flow into the collection chamber;
    engaging means for causing the heating probe and collection assembly to engage the portion of core surface effective for releasing and collecting hydrocarbons from the portion of core surface and thereafter to disengage therefrom; and transport means for causing the core to be transported adjacent the heating probe and collection assembly for being engaged at intervals along the core by said assembly.

17. The apparatus of claim 16 further comprising:

core transport means for causing the core and the heating probe and collection assembly to move relative to one another such that at successive times successive portions of core surface are available for engagement by the heating probe and collection assembly.

18. The apparatus of claim 17 wherein:

the heating probe and collection assembly comprise at least a first and a second heating probe and collection assembly spaced apart;

the first heating probe and collection assembly being at a temperature effective for extracting free hydrocarbons from core, and the second heating probe and collection assembly being at a temperature effective for pyrolyzing kerogen in core.

* * * * *

UNITED STATES PATENT AND TRADEMARK OFFICE
CERTIFICATE OF CORRECTION

PATENT NO.: 5,201,219

DATED: 13 April 1993

INVENTOR(S): Eric L. Bandurski; John W. Kearns; Houston B. Mount

It is certified that error appears in the above-identified patent and that said Letters Patent is hereby corrected as shown below:

| Col. | Line | |
|---|---|---|
| 5 | 3 | "in plan view" should read --in plain view--. |
| 8 | 35 | "surface upon the core" should read --surface, the core--. |

Signed and Sealed this

Twenty-second Day of February, 1994

Attest:

BRUCE LEHMAN

Attesting Officer

Commissioner of Patents and Trademarks